(12) United States Patent
Hüttenberger et al.

(10) Patent No.: US 7,875,861 B2
(45) Date of Patent: Jan. 25, 2011

(54) POSITIONING DEVICE FOR POSITIONING A PATIENT AND METHOD FOR OPERATING A POSITIONING DEVICE

(75) Inventors: Stefan Hüttenberger, Erlangen (DE); Eike Rietzel, Darmstadt (DE)

(73) Assignee: Siemens Aktiengesellschaft, Munich (DE)

( * ) Notice: Subject to any disclaimer, the term of this patent is extended or adjusted under 35 U.S.C. 154(b) by 198 days.

(21) Appl. No.: 12/321,046

(22) Filed: Jan. 15, 2009

(65) Prior Publication Data
US 2009/0184260 A1 Jul. 23, 2009

(30) Foreign Application Priority Data
Jan. 18, 2008 (DE) .................. 10 2008 005 069

(51) Int. Cl.
*A61N 5/01* (2006.01)
*G21K 5/10* (2006.01)
(52) U.S. Cl. ............... 250/491.1; 250/505.1; 250/492.1; 250/442.11; 600/2; 5/601
(58) Field of Classification Search .............. 250/491.1, 250/505.1, 492.1, 442.11; 600/2; 5/601
See application file for complete search history.

(56) References Cited

U.S. PATENT DOCUMENTS 7,786,433 B2 * 8/2010 Gunzert-Marx et al. .. 250/252.1

2005/0234327 A1 * 10/2005 Saracen et al. ............. 600/407
2006/0002511 A1    1/2006 Miller et al.
2008/0219411 A1 *  9/2008 Gunzert-Marx et al. ..... 378/207

FOREIGN PATENT DOCUMENTS

| DE | 69533958 T2    | 6/2005 |
| DE | 102004054867 A1 | 5/2006 |
| DE | 102006002908 B3 | 8/2007 |
| DE | 102006008505 A1 | 8/2007 |
| WO | 2007017211 A2  | 2/2007 |

* cited by examiner

*Primary Examiner*—Nikita Wells

(57) ABSTRACT

The invention relates to a positioning device for positioning a patient in a medical device comprising a patient receiving device for placing a patient and a robot arm having a plurality of movement axes for positioning the patient receiving device in a room. The positioning device can be placed into a manual operating mode in which a position of the patient receiving device in the room can be changed manually. The invention also relates to a method for operating the positioning device, comprising: providing a normal operating mode for positioning the patient receiving device automatically at a position predefined by a control device; providing a manual operating mode for manually changing a position of the patient receiving device; and switching from the normal operating mode into the manual operating mode if a switchover condition is present. The invention further relates to an irradiation device having the positioning device.

14 Claims, 3 Drawing Sheets

POSITIONING DEVICE FOR POSITIONING A PATIENT AND METHOD FOR OPERATING A POSITIONING DEVICE

CROSS REFERENCE TO RELATED APPLICATIONS

This application claims priority of German application No. 10 2008 005 069.5 filed Jan. 18, 2008, which is incorporated by reference herein in its entirety.

FIELD OF THE INVENTION

The invention relates to a positioning device for positioning a patient in a medical diagnostic and/or therapy system, such as is used in particular in a particle therapy system for positioning a patient relative to a treatment beam. The invention also relates to a particle therapy system having a positioning device of said kind as well as to a method for operating a positioning device of said kind.

BACKGROUND OF THE INVENTION

Particle therapy is an established method for treating tissue, in particular tumor diseases. However, irradiation methods as used in particle therapy are also used in non-therapeutic application areas. These include, for example, research activities in the particle therapy field that are carried out on non-living phantoms or bodies, irradiation of materials, etc. Typically, in such applications, charged particles are accelerated to high energies, formed into a particle beam and guided by way of a high-energy beam transport system to one or more irradiation rooms. In one of said irradiation rooms the object that is to be irradiated is exposed to the particle beam. In this case it is essential to the success of an exposure to radiation that the object that is to be irradiated is positioned as accurately as possible relative to the particle beam.

Devices are known in which the positioning of, for example, a patient is accomplished with the aid of a robot-based positioning device. For example, a patient treatment couch can be flexibly positioned relative to a particle beam by means of a multi-axis robot arm.

SUMMARY OF THE INVENTION

It is therefore the object of the invention to disclose a positioning device for positioning a patient in a medical diagnostic and/or therapy device, by means of which positioning device a high level of patient safety is ensured during the positioning of the patient. It is also the object of the invention to disclose an irradiation device which ensures a high level of patient safety during the positioning of the patient as well as a method for operating a positioning device of said kind.

The object of the invention is achieved by a positioning device, an irradiation device, and a method for operating a positioning device as claimed in the independent claims. Advantageous developments can be found in the features of the dependent claims.

The inventive positioning device for positioning a patient in a medical diagnostic and/or therapy device comprises:
  a patient receiving device on which a patient can be placed, and
  a robot arm having a plurality of movement axes and enabling the patient receiving device to be positioned in the room, wherein the positioning device can be placed into a manual operating mode in which a position of the patient receiving device in the room can be changed manually.

The invention is based on the concept that although accurate and precise positioning of a patient is possible with known positioning devices having a multi-axis robot arm, whereby the control of the positioning device is usually handled automatically by a control unit, if necessary by interaction with a user who controls the controller by means of a manual control element, in emergency situations access to a patient can be made more difficult on account of a positioning device of that kind. In an emergency situation, for example in the event of a malfunction of the positioning device and/or of the system in which the positioning device is operated, the robot arm is normally disabled so that it will no longer be possible to move the patient by way of the control unit. This is designed to ensure that in an emergency situation of said kind the robot arm will not be able to execute any erroneous movements which would put the safety of a patient at serious risk.

An emergency situation of the aforesaid kind can occur, for example, if an emergency stop has been actuated in a particle therapy system, as a result of which on the one hand the particle beam and on the other hand the power supply of many components in the treatment room are switched off. Such an emergency situation can also occur, however, if a component of a particle therapy system, for example the positioning device itself, detects a deviation from a normal mode of operation and accordingly is switched to a mode in which the scope of operation of the component and/or of further components is restricted, for example as a result of the power supply being switched off.

It was recognized in such instances that if an emergency situation occurs it is advantageous to at least partially switch off individual and/or multiple components, that as a consequence of doing so, however, the safety of a patient can be compromised, since a disabling of the robot arm of the positioning device may result in the patient's remaining in a position in which an intervention directed at the patient is made more difficult or even impossible. If the positioning device is used in, for example, a gantry-based irradiation room, it is possible—depending on the particular embodiment of the irradiation room—that the irradiation room will have a moving floor which is operated in order to move the gantry out of the irradiation room. In this state the irradiation room has no floor on which a user could walk without risk. If an emergency situation arises at such a time, the positioning device can, for example, block the patient in a position in which access to the patient is impossible. Even in irradiation rooms with a floor present, however, in an emergency situation the patient can be blocked in an unfavorable position of said kind in such a way that access to the patient, for example in order to enable resuscitation measures to be carried out, is impossible.

A simple and effective solution to this problem is provided by means of the positioning device according to the invention. The positioning device is embodied in such a way that it can be placed into a manual operating mode in which a position of the patient receiving device in the room can be at least partially changed manually. In this way it is now possible even in emergency situations to change the position of the patient in the room manually so that a patient can be brought into a more favorable position for recovery or treatment.

The patient receiving device can be embodied e.g. as a patient treatment couch or patient chair on which a patient can be positioned in a posture provided for irradiation.

In an advantageous embodiment of the invention, the positioning device is embodied in such a way that a rotation of the patient receiving device about a vertical axis can be performed manually in the manual operating mode. This can be realized, for example, such that in the case of the multi-axis robot arm one axis or more than one axis, each with a vertical axis of rotation, can be unlocked or, as the case may be, released. A rotation about one vertical axis of rotation is usually sufficient to recover a patient placed on the patient receiving device from a risk situation. The unlocking of an axis (or more than one axis) can easily be realized e.g. by selective unlocking of the brakes of an axis in the manual operating mode.

In one embodiment, the positioning device is embodied in such a way that the manual operating mode is activated automatically if a fault condition occurs during normal operation of the positioning device and/or the diagnostic and/or therapy system. A fault condition indicates a malfunction, so that in that case various steps are usually taken in order to ensure the safety of the patient. In a particle therapy system, for example, the particle beam can be switched off in order to stop an irradiation process. In this embodiment, in addition, the positioning device is now placed automatically into the manual operating mode in order to permit a manual movement of the patient receiving device and hence of the patient at all times in the event of a fault condition being present.

In an alternative and/or additional embodiment, the positioning device has a manually actuatable switchover device. An actuation of the switchover device places the positioning device into the manual operating mode. By this means it is possible to activate the manual operating mode of the positioning device by manual intervention. In this way a patient can be brought more quickly into a desired position than would be possible, for example, in the case of a normal, automatically controlled movement of the positioning device during operation. A normal movement of the positioning device is namely often linked to the movement of other components in the treatment room, with the result that in an automatically controlled movement of the positioning device individual movements have to be coordinated with one another, an operation which often takes up a considerable amount of time. By means of a manual actuation of the switchover device it is possible when necessary to switch to the manual operating mode so that a patient can quickly be moved manually.

This can be realized, for example, in that a button disposed on the positioning device is pressed, thereby, for example, unlocking a specific axis of the robot arm. In another embodiment, the switchover device can be embodied in such a way that the switchover device is disposed on one of the movement axes of the robot arm, in particular on a movement axis having a vertical axis of rotation, and an actuation of the switchover device effects a direct mechanical unlocking of said movement axis. This is particularly advantageous since in this way an unlocking of the movement axis is possible in any case, even if the control of the positioning device has failed completely.

In one embodiment, in order to simplify moving of the patient receiving device, means for manually taking hold of the patient receiving device are disposed on the patient receiving device. Means of said kind can be, for example, a handle or a receiving device into which a hook disposed on a pole can be introduced. A cord that extends from the patient receiving device as far as a user enables the patient receiving device to be moved even when it is not located within immediate reach of a user. The cord can be, for example, permanently attached to the robot arm and released when necessary by pulling.

The irradiation device according to the invention comprises:
   a particle source for generating particles,
   an accelerator for accelerating the particles and for providing a high-energy particle beam,
   an irradiation room for exposing an object that is to be irradiated to the high-energy particle beam, and
   a positioning device as claimed in one of claims 1 to 7 which is disposed in the irradiation room.

In a special embodiment, the irradiation room includes a movable gantry, thereby enabling the particle beam to be directed from different selectable directions onto the object that is to be irradiated, as well as a removable floor in the irradiation room, in particular in the gantry area of the irradiation room. With the aid of the removable floor, additional freedom of movement can be created for moving the gantry. In a room of this kind the use of the inventive positioning device has a particularly advantageous effect since in this instance—in the case of the positioning device becoming blocked in the area of the removed floor—it would otherwise be possible to recover a patient only with very great effort.

With the inventive method for operating a positioning device by means of which a patient can be positioned in a medical diagnostic and/or therapy system:
   a normal operating mode is provided during which the patient receiving device is positioned fully automatically at a position predefined by means of a control device,
   a manual operating mode is provided during which the position of the patient receiving device in the room can be changed manually, and
   a switchover from the normal operating mode into the manual operating mode is performed as soon as a switchover condition is present.

In one embodiment, a switchover condition can automatically be present in the case of the method whenever a fault condition is detected during the normal operating mode. In this case the fault condition can, for example, characterize a malfunction of the positioning device or else also indicate a malfunction of the medical diagnostic and/or therapy system.

In another embodiment, the switchover condition is present whenever a switchover device has been actuated manually. The switchover device can be, for example, an emergency stop switch, as a result of the actuation of which a series of operations is triggered, an interruption of the irradiation process, for example. The switchover from the normal operating mode into the manual operating mode is accomplished by actuation of the switchover device.

In a special embodiment, the switchover device can, however, also be disposed on a movement axis of the robot arm. In particular, a direct mechanical unlocking of the movement axis of the robot arm is possible by actuating the switchover device.

BRIEF DESCRIPTION OF THE DRAWINGS

Embodiments of the present invention together with advantageous developments in accordance with the features of the dependent claims are explained in more detail with reference to the following drawing, though the invention is not restricted thereto.

DETAILED DESCRIPTION OF THE INVENTION

Figure 1:
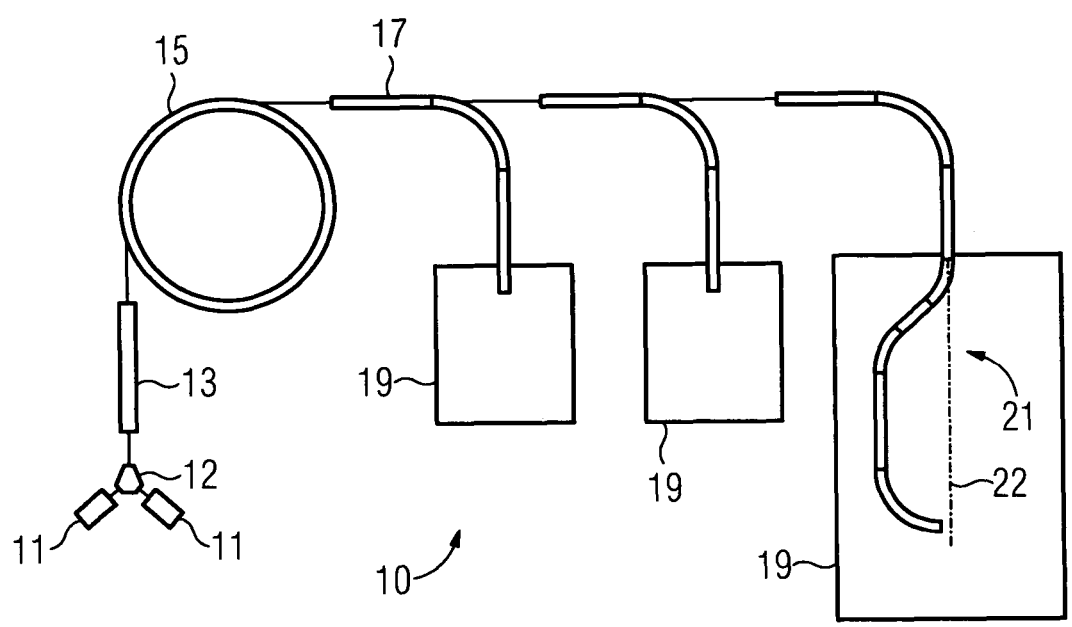
FIG. 1 shows a schematic overview of a particle therapy system.

FIG. 1 shows a schematic overview of the layout of a particle therapy system 10. In a particle therapy system 10, a body, in particular tumor-diseased tissue, is irradiated in particular with a particle beam.

Ions such as, for example, protons, pions, helium ions, carbon ions or other types of ions are principally used as particles. Particles of said kind are typically generated in a particle source 11. If, as shown in FIG. 1, two particle sources 11 are present which generate two different types of ions, it is possible to switch between said two types of ions within a short time interval. For that purpose a switching magnet 12, for example, is used which is disposed between the ion sources 11 on the one side and a pre-accelerator 13 on the other. By this means the particle therapy system 10 can be operated, for example, with protons and with carbon ions simultaneously.

The ions generated by the ion source or one of the ion sources 11 and where applicable selected by means of the switching magnet 12 are accelerated to a first energy level in the pre-accelerator 13. The pre-accelerator 13 is, for example, a linear accelerator (LINAC). The particles are then fed into an accelerator 15, for example a synchrotron or cyclotron. In the accelerator 15, they are accelerated to high energies, such as are required for irradiation. After the particles have exited the accelerator 15, a high-energy beam transport system 17 guides the particle beam to one or more irradiation rooms 19. In an irradiation room 19, the accelerated particles are directed onto a body that is to be irradiated. Depending on embodiment, this is done from a fixed direction (in what are termed "fixed beam" rooms) or else from different directions by way of a rotatable gantry 21 that is movable about an axis 22.

The basic layout of a particle therapy system 10 as shown with reference to FIG. 1 is typical of many particle therapy systems, but can also differ herefrom; for example, depending on the acceleration of the particles, an irradiation device does not have to be disposed as a particle therapy system.

The exemplary embodiments described hereinafter can be used both in connection with the particle therapy system illustrated with reference to FIG. 1 and with other particle therapy systems or radiotherapy systems.

Figure 2:
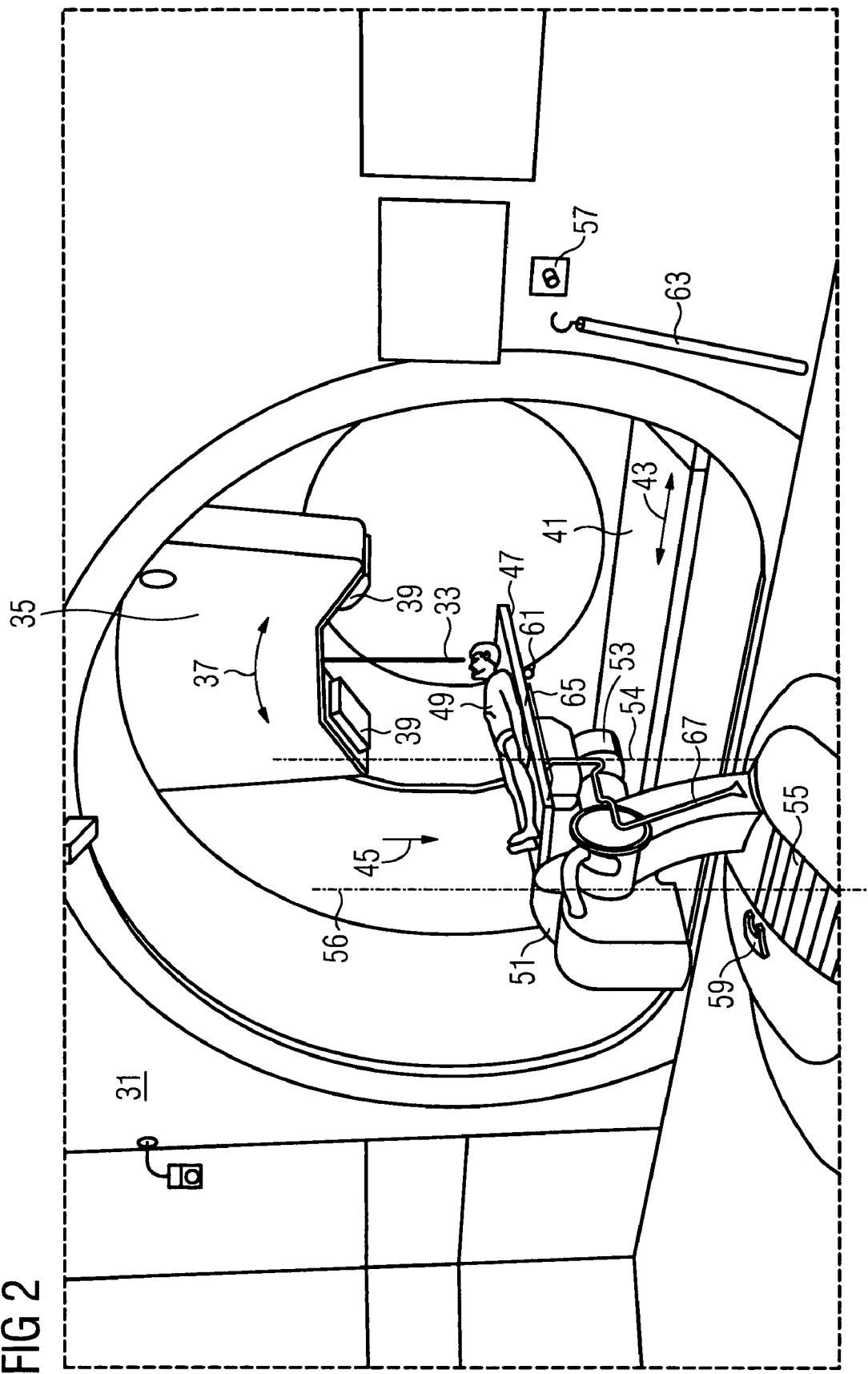
FIG. 2 shows a perspective view of a gantry-based irradiation room having a positioning device.

FIG. 2 shows a perspective view of a gantry-based irradiation room 31 in which a positioning device 45 is used for positioning a patient 49.

The patient 49 is irradiated with a particle beam 33 that is emitted from a particle beam emitting device 35. The particle beam emitting device 35 is disposed on a gantry (not visible in FIG. 2) which enables the particle beam emitting device 35 to be rotated (double-headed arrow 37) in the irradiation room in such a way that the particle beam 33 can be emitted from a plurality of angles. Also disposed on the particle beam emitting device 35 shown are flat-panel detectors 39 which can be used for checking the position of the patient 49 in the irradiation room 31. In order to enable the particle beam emitting device 35 to be positioned in an angular range of preferably 0° to 360°, a part of the floor 41 in the irradiation room 31 can be moved out of the irradiation room 31 (straight double-headed arrow 43). This creates space for the rotation of the gantry, with the result that the particle beam emitting device 35 can also be positioned, for example, such that the particle beam 33 is directed onto a patient 49 from below.

The positioning device 45 is embodied as a multi-axis robot arm 51 by means of which a patient receiving device 47, in this case shown as a patient treatment couch, can be positioned in the irradiation room 31. Instead of a patient treatment couch 47 it is also possible to use, for example, a patient chair on which the patient 49 can be placed in a sitting posture. Not shown in the figure is a control device by means of which the positioning device 45 is operated in order, for example, to move a patient 49 automatically to a predefined position.

A first movement axis 53 of the robot arm 51 enables the patient receiving device 47 to be rotated about a first vertical axis of rotation 54. A second movement axis 55 enables the patient receiving device 47 to be rotated about a second vertical axis of rotation 56. In this case the first movement axis 53 is disposed immediately beneath the patient receiving device 47, while the second movement axis 55 is disposed on the floor of the irradiation room 31. A rotation about the first vertical axis of rotation 54 only rotates the patient receiving device 47. A rotation about the second vertical axis of rotation 56 rotates the entire robot arm 51 together with the patient receiving device 47 about the second vertical axis of rotation 56.

The positioning device 45 is embodied in such a way that it can be placed into a manual operating mode which permits a rotation of the patient receiving device 47 about the first vertical axis of rotation 54 and/or about the second vertical axis of rotation 56 to be performed manually. This can be accomplished for example in that a user (not shown) takes hold of a handle 65 of the patient receiving device 47 and exerts force onto the patient receiving device 47. Alternatively and/or in addition, a user can catch an eye 61 of the patient receiving device 47 by means of a pole 63 that has a hook and exert force onto the patient receiving device 47. A further possibility is to release a cord 67 disposed on the robot arm 51 and exert a pull on the patient receiving device 47 by way of the cord 67.

In an emergency situation this allows the patient 49 to be moved by means of the patient receiving device 47 in such a way that he or she can be brought manually into a position in which care of the patient 49 can be carried out better and more easily. This is the case in particular when the floor 41 of the gantry-based irradiation room 31 has been moved out of the irradiation room 31, thereby making it impossible for a direct approach to be made to the patient 49 positioned in the region of the particle beam emitting device 35. In particular when an emergency situation arises, for example when an emergency stop button 57 has been pressed by means of which both an irradiation process is aborted and automatic control of the position of the particle beam emitting device 35 and of the positioning device 47 is switched off because an unforeseen event has occurred, the patient 49 can easily be recovered from a danger zone manually without its being necessary to restart the system first in order to execute an automatic control of the positioning device 47.

For this purpose the first movement axis 53 and/or the second movement axis 55 of the robot arm 51 can be released, for example, automatically when the emergency stop button 57 has been pressed. Alternatively and/or in addition, a movement axis can be released by direct actuation of a lever that is disposed on the movement axis. In FIG. 2, for example, there is disposed on the second movement axis 55 a lever 59, by the actuation of which the movement axis 55 can be directly unlocked mechanically, such that a movement of the robot arm about said movement axis is made possible manually.

Figure 3:
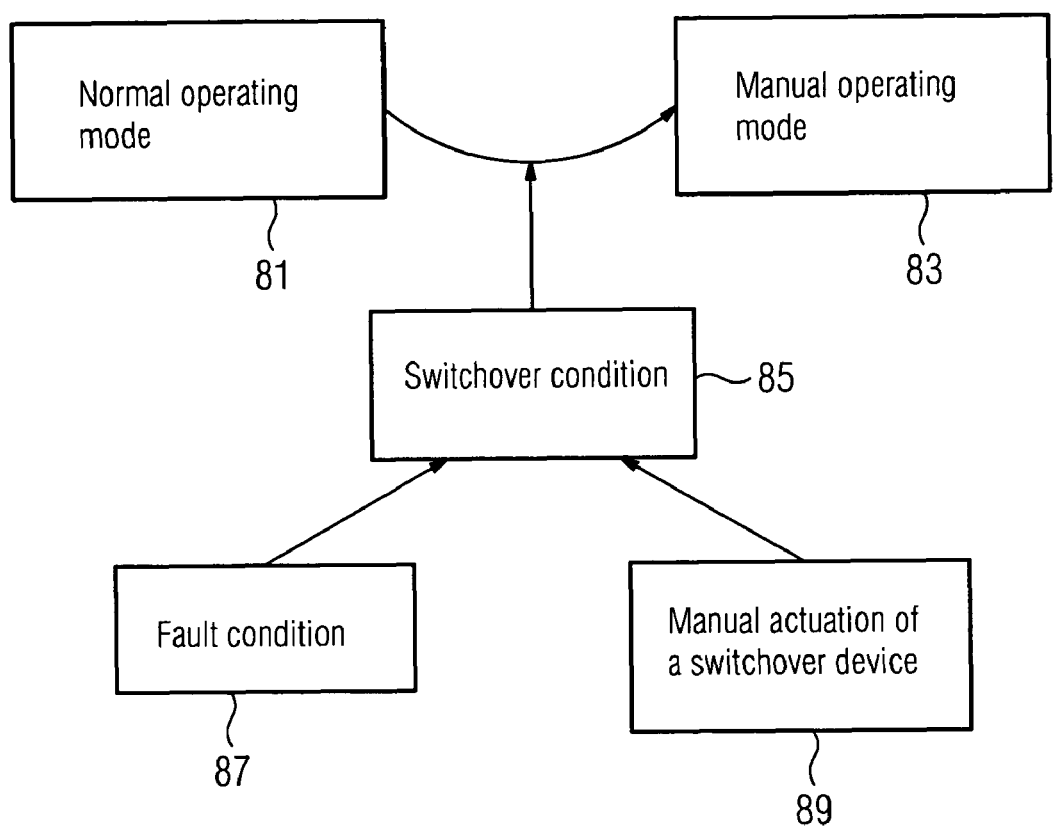
FIG. 3 shows an overview of method-related steps that are performed during operation of the positioning device.

FIG. 3 shows a schematic overview of method-related steps that are performed when operating the positioning device.

The positioning device can be operated in a normal operating mode 81 in which a completely automatic positioning of a patient by means of the positioning device is performed. Manual positioning of the positioning device is not possible in the normal operating mode 81. The positioning device can also be operated in a manual operating mode 83 in which a manual positioning of the positioning device, in particular of the patient receiving device, is made possible in the room.

During the operation of the positioning device it is possible to switch from the normal operating mode 81 into the manual operating mode 83 as soon as a switchover condition 85 is present. Depending on the embodiment of the positioning device, a switchover condition 85 of said kind can automatically be present when a fault condition 87 has been detected during the operation of the positioning device, the condition being caused, for example, by a malfunction of the positioning device itself or by a malfunction of the diagnostic and/or therapy system in which the positioning device is operated.

A switchover condition 85 can alternatively and/or additionally be present also when a manual actuation 89 of a switchover device has been performed. A switchover device of said kind can be, for example, the emergency stop button 57 shown in FIG. 2, by the actuation of which the switchover condition has been triggered manually, as a result of which the positioning device is placed into the manual operating mode, or, for example, a lever 59 which can be pulled.

The invention claimed is:

1. A positioning device for positioning a patient in a medical device, comprising:
    a patient receiving device on which the patient is placed;
    a robot arm having a plurality of movement axes that changes a position of the patient receiving device; and
    a switchover device that switches the positioning device from a normal operating mode for automatically changing the position of the patient receiving device into a manual operating mode for manually changing the position of the patient receiving device.

2. The positioning device as claimed in claim 1, wherein the manual operating mode comprises a rotation of the patient receiving device about a vertical axis of the rotation.

3. The positioning device as claimed in claim 1, wherein at least one of the movement axes is unlocked in the manual operating mode so that the robot arm is moved manually about the at least one of the movement axes.

4. The positioning device as claimed in claim 1, wherein the manual operating mode is activated automatically if a fault condition occurs during the normal operation mode.

5. The positioning device as claimed in claim 1, wherein the switchover device is manually actuatable.

6. The positioning device as claimed in claim 1, wherein the switchover device is disposed on one of the movement axes of the robot arm for mechanically unlocking the one of the movement axes.

7. The positioning device as claimed in claim 1, wherein the patient receiving device comprises a device for manually holding and moving the patient receiving device.

8. An irradiation device, comprising:
    a particle source that generates particles;
    an accelerator that accelerates the particles and provides a high-energy particle beam;
    an irradiation room where a patient to be irradiated to the high-energy particle beam is exposed; and
    a positioning device that comprises:
        a patient receiving device on which the patient is placed,
        a robot arm having a plurality of movement axes that changes a position of the patient receiving device, and
        a switchover device that switches the positioning device from a normal operating mode for automatically changing the position of the patient receiving device into a manual operating mode for manually changing the position of the patient receiving device.

9. The irradiation device as claimed in claim 8, wherein the irradiation room comprises:
    a movable gantry for directing the high-energy particle beam from different selectable directions onto the patient, and
    a removable floor.

10. A method for operating a positioning device of a medical device comprising a patient receiving device and a robot arm having a plurality of movement axes, comprising:
    providing a normal operating mode of the positioning device in which the patient receiving device is positioned automatically at a position;
    providing a manual operating mode of the positioning device in which the position of the patient receiving device is changed manually; and
    switching from the normal operating mode into the manual operating mode if a switchover condition is present.

11. The method as claimed in claim 10, wherein the manual operating mode comprises a rotation of the patient receiving device about a vertical axis of the rotation.

12. The method as claimed in claim 10, wherein the switchover condition is automatically present if a fault condition is detected in the normal operating mode.

13. The method as claimed in claim 10, wherein the switchover condition is present following a manual actuation of a switchover device that switches the positioning device from the normal operating mode into the manual operating mode.

14. The method as claimed in claim 13, wherein the actuation of the switchover device comprises a mechanical unlocking of one of the movement axes of the robot arm.

* * * * *